United States Patent [19]

Falb et al.

[11] Patent Number: 4,693,853

[45] Date of Patent: Sep. 15, 1987

[54] ANESTHETIC VAPORIZER

[75] Inventors: Wolfgang Falb, Krummesee; Martin Ryschka, Stockelsdorf; Carl-Friedrich Wallroth, Lübeck, all of Fed. Rep. of Germany

[73] Assignee: Drägerwerk Aktiengesellschaft, Fed. Rep. of Germany

[21] Appl. No.: 879,326

[22] Filed: Jun. 27, 1986

[30] Foreign Application Priority Data

Jul. 4, 1985 [DE] Fed. Rep. of Germany ....... 3523947

[51] Int. Cl.⁴ ................................................ B01F 3/04
[52] U.S. Cl. .............................. 261/39.1; 128/202.27; 128/203.14; 128/203.25; 128/204.13; 261/96; 261/99; 261/105; 261/DIG. 65
[58] Field of Search ...................... 128/202.27, 203.14, 128/203.25, 204.13; 261/39.1, DIG. 65, 96, 99, 105

[56] References Cited

U.S. PATENT DOCUMENTS

| 3,038,472 | 6/1962 | Gaylord | 128/202.27 |
|---|---|---|---|
| 3,486,730 | 12/1969 | Potash | 128/202.27 |
| 3,534,732 | 10/1970 | Bickford | 128/203.14 |
| 3,831,599 | 8/1974 | Needham | 128/203.12 |
| 4,017,566 | 4/1977 | Seidel | 128/203.14 |
| 4,267,974 | 5/1981 | Kienholz et al. | 128/203.25 |
| 4,346,701 | 8/1982 | Richards | 128/200.19 |
| 4,444,182 | 4/1984 | Gregory | 128/203.14 |

FOREIGN PATENT DOCUMENTS

| 2507261 | 5/1978 | Fed. Rep. of Germany . | |
| 964414 | 7/1964 | United Kingdom | 128/203.25 |

Primary Examiner—Tim Miles
Attorney, Agent, or Firm—McGlew and Tuttle

[57] ABSTRACT

An anesthetic vaporizer with a vaporizer chamber into which leads a gas inlet channel for fresh gas and which is connected via an outlet channel with a proportioning unit containing setting means for the anesthetic concentration to be released to the fresh gas is to be improved in such a way that exchanging the various anesthetics is made possible to only a single proportioning unit. The vaporizer chamber is a self-enclosed housing part to be coupled to the proportioning unit via connectors and the setting means are adjustable to the release of the respective anesthetic used.

5 Claims, 2 Drawing Figures

000
ANESTHETIC VAPORIZER

FIELD AND BACKGROUND OF THE INVENTION

This invention relates in general to vaporizers and in particular to a new and useful anesthetic vaporizer having an exchangeable vaporizer chamber.

The invention relates in general to liquid vaporizers and in particular to a new and useful anesthetic vaporizer with a vaporizer chamber into which a gas inlet channel for fresh gas leads and which is connected via an outlet channel with a proportioning unit containing setting means for the anesthetic concentration to be released to the fresh gas.

A similar anesthetic vaporizer has become known through German OS No. 25 07 261.

In anethesis apparatus, anesthetic vaporizers are inserted in the fresh has cycle in order to enrich the fresh gas to be suppliedd to the patient with a desired anesthetic of different, adjustable concentration. For this purpose, the fresh gas line is connected to the anesthetic vaporizer, and a partial stream of fresh gas in branched off into the vaporizer chamber via a line, while the other part is conducted via a by-pass line. The vaporizer chamber stream is saturated with anesthetic vapor and rejoins the fresh gas partial stream from the by-pass line. By setting a control valve in the vaporizer chamber stream, the proportion of the vaporizer chamber steam to the by-pass stream is varied, whereby the desired anesthetic concentration in the fresh gas stream can be adjusted. In the path of the by-pass stream a temperature-dependent control unit extending into the vaporizer chamber is disposed which compensates the temperature influence and permits constant proportioning at different operating temperatures. The anesthetic concentration can be read by means of an indicating unit designed as a scale ring whose position is variable in accordance with the setting of the control valve. After the partial streams have been brought together, the fresh gas enriched with anesthetic is introduced via a gas mixture outlet channel into the respiration system leading to the patient.

In the known anesthetic vaporizer, the vaporizer chamber is firmly connected with the proportioning unit, as one must use a proportioning unit correlated with the particular anesthetic used. Because of the different vapor pressure and different viscosity of the various anesthetics, an identical setting of the control valve leads to different anesthetic concentrations in the fresh gas stream supplied to the patient. Therefore, if during an anesthesia it is necessary to change the anesthetic, the known anesthetic vaporizer plus its proportioning unit must be exchanged in its entirety. Emptying the known vaporizer and subsequently filling it with another anesthetic is not possible, as the inner walls of the vaporizer chamber, and in particular the wicks used for vaporization, are impregnated with the old anesthetic, which would become mixed with the new anesthetic in an uncontrollable manner. For the application of several anesthetics during an anesthesis to be carried out, it is necessary, therefore, to provide a separately calibrated anesthetic vaporizer of the known kind for each anesthetic and to keep it in readiness during performance of the anesthesia. This means considerable cost of manufacture and procurement. Moreover, as a rule, an appropriate receiving space for several anesthetic vaporizers for different anesthetics is provided for this purpose at the apparatus. Therefore, several vaporizers must be connectable to an apparatus using the known vaporizer. If these vaporizers are to be ready and connected during use of the apparatus, a separate supply line for fresh gas and gas mixture for each vaporizer as well as space for accommodating several vaporizers must be provided. These measures increase the weight of an anesthesia apparatus considerably, complicate its handling, and require much space.

SUMMARY OF THE INVENTION

The present invention provides an improved anesthetic vaporizer in which even when using different anesthetics, the same proportioning unit can be used, requiring space and the connections for only one vaporizer in the anesthesia apparatus.

The vaporizer chamber is formed as a self-enclosed housing part to be coupled to the proportioning unit via connecting pieces, and the setting means can be adapted to the release of the respective anesthetic used.

The advantage obtained with the invention resides mainly in that when changing to a new anesthetic it suffices to separate the vaporizer chamber containing the anesthetic and the wick needed for vaporization from the proportioning unit and that a vaporizer chamber filled with the new anesthetic can be applied to the proportioning unit remaining at the apparatus. Besides the saving due to the multiple use of the proportioning unit, space for only one vaporizer needs to be provided at the apparatus for this purpose. Thus it is possible to dose several anesthetics with only one proportioning unit in combination with different vaporizer chambers. The closed desing of the vaporizer chamber permits transport of the removed vaporizer chamber without a possibility that residues of anesthetics left in it could be released to the environment. The uncoupled vaporizer chambers can be stored separately from the proportioning unit, so that storage space is saved.

Preferably the connecting pieces are laid out so that they come in engagement with the gas inlet channel for fresh gas and with the outlet channel. It is appropriate to seal the openings of the two channels with the vaporizer chamber removed, for example by means of ball valves which, when the vaporizer chamber is being coupled to the proportioning unit, are pressed on by respective stay bolts engaging in the ball valves. To this end the stay bolts contain corresponding bores for the gas inlet chananels and for the outlet channel as connection guides between the vaporizer chamber and the proportioning unit. At the circumference of the stay bolts seal rings are disposed, which seal the gas inlet channel and the outlet channel of the vaporizer chamber from the atmosphere before tha ball valves are opened.

Adaptation of the setting means to the required release of the anesthetic used can take place in several ways. Preferably it is done by way of a marking which engages in the proportioning unit and thus indicates to the user of the vaporizer, with the vaporizer chamber coupled, which anesthetic is being supplied to the proportioning unit.

Appropriately the marking is in the form of marking pins which engage at an axially displaceable scale drum for the concentration adjustment of the anesthetics to be proportioned. Applied on the outer circumference of the scale drum are various axially spaced concentration scales correlated with the particular anesthetics to be proportioned. When the vaporizer chamber is being coupled to the proportioning unit, the marking pins release a scale which corresponds to the anesthetic contained in the chamber and which shows during actuation of the proportioning unit the concentration information applicable to the respective anesthetic. Color backing of the various scales or a scale provided with the designation of the respective anesthetic facilities recognizing the particular anesthetic.

Another simple identification may consist in that by appropriate electric coding pins electric signal units correlated with the various anesthetics, such as color bulbs or characters, are activated when the vaporizer chamber is coupled to the proportioning unit.

The marking can also act on the proportioning unit with suitable means in such a way that in the unit, for example the transmission ratio of a gear is changed at the transmission elements for adjustment of the control valve, depending on which vaporizer chamber is connected.

If a temperature-dependent control system forms part of the proportioning unit, it can advantageously be used for all connectable vaporizer chambers in an equivalent manner. The construction of the vaporizer chamber itself becomes simpler, easier and more cost-effective. It suffices to provide in it merely simple heat conduction elements in the form of heat conduction sheets or blocks. These form the heat contact of the vaporized anesthetic to an intermediate plate which serves, when the chamber is connected, as a connecting piece to the proportioning unit, and when the chamber is disconnected, as the housing closure thereof.

The temperature-dependent control systems may be known mechanically operated or electrically controlled ones. If, for example, an electrically actuated control valve disposed in the by-pass stream is used, its actuation occurs appropriately via a temperature sensor. It extends into the vaporizer chamber and sends a signal corresponding to the temperature to the proportioning unit. The connection of the temperature sensor with the proportioning unit occurs by way of an electrical point of separation.

Accordingly it is an object of the invention to provide an anesthetic vaporizer which includes a vaporizer housing having an interior liquid anesthetic reservoir and which is closed by a plate on its outside which is provided with a plurality of receiving openings into which stay bolts of a proportioning unit is engageable, the proportioning unit have an adjustable setting arrangement for setting release of the respective anesthetic used.

A further object of the invention is to provide an anesthetic vaporizer which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
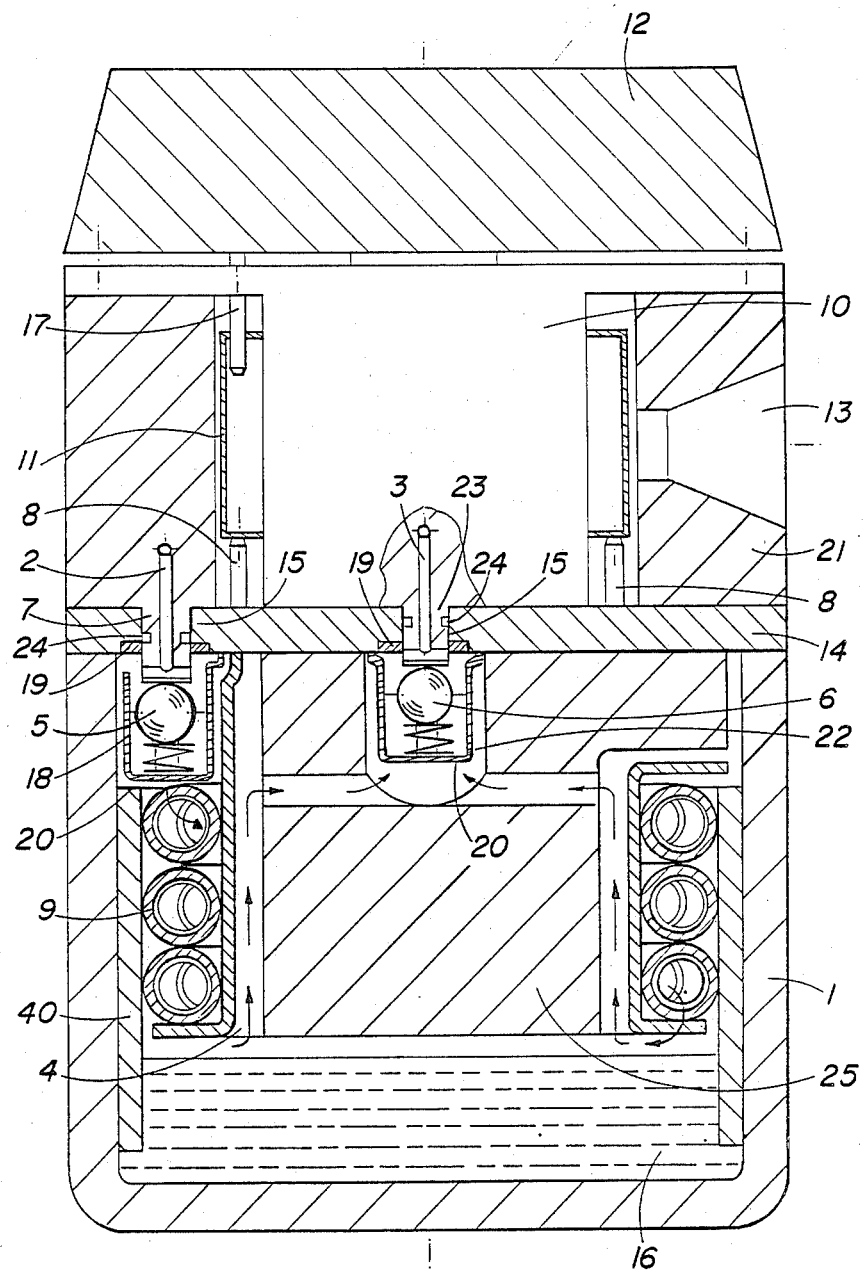
FIG. 1 is a section through the vaporizer chamber and proportioning unit constructed in accordance with the invention.

Referring to the drawings in particular the invention embodies therein comprises an anesthetic vaporizer including a portion defining a vaporizer chamber 1 with anesthetic 16 therein. The chamber is closed by an intermediate plate 14 which has a plurality of receiving openings 15 to receive staples 7 and 23 of a proportioning unit 10. The construction is thus that a flow passage is defined between gas inlet 2 to the reservoir of the liquid 16 indicated by the gas feed 4 shown by the arrows.

FIG. 1 shows an anesthetic vaporizer which comprises a proportioning unit 10 in a proportioning housing 21 and of a vaporizer chamber 1 which is coupled to the proportioning unit 10 through stay bolts 7 and 23. The proportioning unit 10 can be set with a handwheel 12. From the proportioning housing 21 a gas inlet channel 2 leads the vaporizer chamber stream into the guide cage 18 of a seal element in the form of a ball valve 5 which in the state shown is open and held against the stay bolt 7 by a spring 20. The interior of the guide housing 18 is connected with the tubular wick 9 which absorbs the liquid anesthetic 16 via the wick jacket 40. The vaporizer chamber stream saturated with the vaporized anesthetic from the liquid anesthetic 16 is conducted via the anesthesia gas feed 4 to an additional cage 22, which contains a seal element likewise in the form of a ball valve 6. The anesthesia gas feed 4 leads into the interior of cage 22 and continues via the outlet channel 3 inside the additional stay bolt 23, which leads into the proportioning unit 10.

Inside the proportioning unit 10, the outlet channel 3 returns the vaporizer chamber stream into the fresh gas line. The vaporizer chamber 1 is closed off from the proportioning unit 10 by an intermediate plate 14, with the openings 15 necessary for the stay bolts 7, 23. At the stay bolts 7, 23 an O-ring seal 24 is provided; they seal the interiors of the guide housing 18, 22 from the surrounding. In the surface of the intermediate plate 14 toward the vaporizer chamber 1, around the openings 15, valve seats 19 are arranged, on which rest the ball valves 5 and 6 when the vaporizer chamber 1 is removed. Protruding from the intermediate plate at its surface toward the proportioning unit 10 are marking pins 8, by which the scale drum 11 is brought into a position such that a display scale (not shown) corresponding to the respective anesthetic 16 appears in the viewing window 13. The scale drum 11 is arranged rotatably relative to the proportioning unit 10 and is connected with the handwheel 12 through the driver pin 17 protruding into it.

For better heat conduction, the vaporizer chamber 1 contains heat conduction elements 25 which are in contact with the proportioning unit 10 via the intermediate plate 14.

Figure 2:
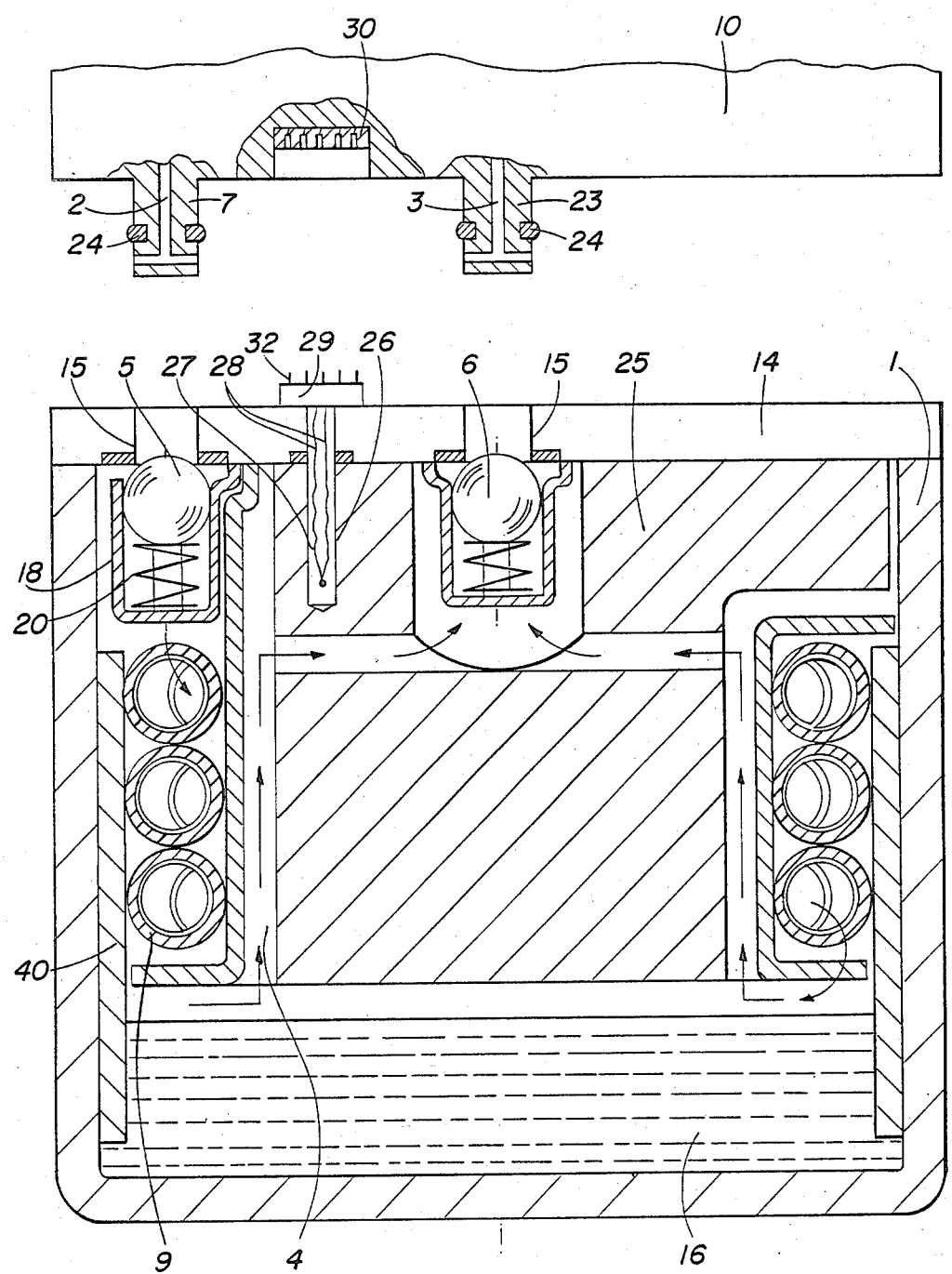
FIG. 2 is a view of the unit with the uncoupled vaporizer chamber.

In FIG. 2 shows the vaporizer chamber 1 removed from the proportioning unit 10. Like parts shown also in FIG. 1 bear the same numbers. In the intermediate plate 14, to a limited depth, a bore 26 is formed in the heat conduction element 25. Bore 26 contains a temperature sensor 27, the connecting lines 28 of which are connectd with a coupling piece 29. In the connected state of the vaporizer chamber 1, the coupling piece 29 engages into the connecting piece 30 at the proportioning unit 10.

The coupling piece 29 and connecting piece 30 thus form an electrical point of separation at which are contained via pin contacts 32 not only the connecting lines 28, but also additional contacts for actuation of an electrical marking for the various usable anesthetics.

While a specific embodiment of the invention has been shown and described in detail to illustrate the application of the principles of the invention, it will be understood that the invention may be embodied otherwise without departing from such principles.

What is claimed is:

1. An anesthetic vaporizer, comprising a vaporizer housing having an interior liquid anesthetic reservoir, an intermediate plate closing said housing having a plurality of receiving openings, a proportioning unit having fluid transmitting projections of corresponding numbers as the openings, said fluid transmitting projections being positionedd to engage into the openings upon joining of the proportioning unit to the vaporizer housing, a flow passage being defined from a gas inlet to said reservoir through said fluid transmitting projection to a flow passage extending back into said proportioning unit, and a gas setting unit in said propprtioning unit adapted to the release of the respective anesthetic used, marking means engaging into the proportioning unit for adaption of the setting means in said unit, said marking means being in the form of a marking pin and said gas setting means including a scale means for providing an indication of the anesthetic, operatively connected in said proportioning unit so as to be displaceable in an axial direction.

2. An anesthetic vaporizer according to claim 1, wherein said openings and said projections provide a valve passage including an inlet for the inlet flow of the anesthetic and an outflow for the outflow of the anesthetic.

3. An anesthetic vaporizer according to claim 2, wherein said valve elements comprise ball valves, and spring means urging said ball valves in a closing direction aganist valve seat.

4. An anesthetic vaporizer, comprising: a vaporizer housing having an interior liquid anesthetic reservoir; an intermediate plate closing said housing having a plurality of receiving openings; a proportioning unit having fluid transmitting projections of corresponding numbers as the openings, said fluid transmitting projections being positioned to engage into the openings upon joining of the proportioning unit to the vaporizer housing; a flow passage being defined from a gas inlet, associated with said housing, to said reservoir through said fluid transmitting projections to a flow passage extending back into said proportioning unit; a gas setting unit in said proportioning unit adapted to the release of the respective anesthetic used; a temperature dependent control system, in said proportioning unit, said temperature dependent control system including a heat conduction element in said vaporizing housing, in intimate contact with said intermediate plate.

5. An anesthetic vaporizer, comprising: a vaporizer housing having an interior liquid anesthetic reservoir; an intermediate plate closing said housing having a plurality of receiving openings, a proportioning unit having fluid transmitting projections of corresponding numbers as the openings, said fluid transmitting projections being positioned to engage into the openings upon joining of the proportioning unit to the vaporizer housing; a flow passage being defined from a gas inlet to said reservoir through said fluid transmitting projections to a flow passage extending back into said proportioning unit; a gas setting unit in said proportioning unit adapted to the release of the respective anesthetic used; and, an electrically controlled temperature dependent control system being formed as part of said proportioning unit and including a temperature sensor protruding into the vaporizer chamber and being connected with a proportioning unit via an electrical point of separation.

* * * * *